United States Patent
Kintz et al.

(10) Patent No.: US 11,504,035 B2
(45) Date of Patent: Nov. 22, 2022

(54) APPARATUS AND METHODS FOR DETECTING OPTICAL SIGNALS FROM IMPLANTED SENSORS

(71) Applicant: Profusa, Inc., South San Francisco, CA (US)

(72) Inventors: Gregory J. Kintz, Santa Cruz, CA (US); William A. McMillan, La Honda, CA (US); Natalie A. Wisniewski, San Francisco, CA (US)

(73) Assignee: Profusa, Inc., Emeryville, CA (US)

( * ) Notice: Subject to any disclaimer, the term of this patent is extended or adjusted under 35 U.S.C. 154(b) by 136 days.

(21) Appl. No.: 16/291,268

(22) Filed: Mar. 4, 2019

(65) Prior Publication Data
US 2020/0008716 A1      Jan. 9, 2020

Related U.S. Application Data

(63) Continuation of application No. 14/297,787, filed on Jun. 6, 2014, now Pat. No. 10,219,729.

(60) Provisional application No. 61/832,078, filed on Jun. 6, 2013, provisional application No. 61/832,065, filed on Jun. 6, 2013.

(51) Int. Cl.
| | | |
|---|---|---|
| *A61B 5/1455* | (2006.01) | |
| *A61B 5/1459* | (2006.01) | |
| *A61B 5/00* | (2006.01) | |
| *A61B 5/145* | (2006.01) | |

(52) U.S. Cl.
CPC .......... *A61B 5/1459* (2013.01); *A61B 5/0017* (2013.01); *A61B 5/14532* (2013.01); *A61B 2562/0233* (2013.01); *A61B 2562/043* (2013.01)

(58) Field of Classification Search
None
See application file for complete search history.

(56) References Cited

U.S. PATENT DOCUMENTS

| | | | |
|---|---|---|---|
| 4,703,756 A | 11/1987 | Gough et al. | |
| 5,094,958 A | 3/1992 | Klainer et al. | |
| 5,284,140 A | 2/1994 | Allen et al. | |
| 5,462,880 A | 10/1995 | Kane et al. | |
| 5,551,422 A * | 9/1996 | Simonsen | A61B 5/14532 |
| | | | 600/322 |
| 5,777,060 A | 7/1998 | Van Antwerp | |

(Continued)

FOREIGN PATENT DOCUMENTS

| | | |
|---|---|---|
| CN | 1790245 | 6/2006 |
| CN | 102811657 A | 12/2012 |

(Continued)

OTHER PUBLICATIONS

Examination Report for Canadian Application No. 2913474, dated Jun. 19, 2020, 4 pages.

(Continued)

*Primary Examiner* — Marjan Fardanesh
(74) *Attorney, Agent, or Firm* — Cooley LLP

(57) ABSTRACT

Some embodiments described herein relate to an apparatus including a light source configured to transmit an excitation optical signal to an implanted sensor and a detector configured to detect an analyte-dependent optical signal emitted from an implanted sensor. The apparatus can include a lens configured to focus at least a portion of the analyte-dependent optical signal onto the detector.

9 Claims, 11 Drawing Sheets

(56) References Cited

U.S. PATENT DOCUMENTS

| | | |
|---|---|---|
| 5,895,658 A | 4/1999 | Fossel |
| 5,962,852 A | 10/1999 | Knuettel et al. |
| 6,002,954 A | 12/1999 | Van Antwerp et al. |
| 6,011,984 A * | 1/2000 | Van Antwerp ..... A61B 5/14532 600/310 |
| 6,013,122 A | 1/2000 | Klitzman et al. |
| 6,040,194 A | 3/2000 | Chick et al. |
| 6,104,945 A | 8/2000 | Modell et al. |
| 6,175,752 B1 | 1/2001 | Say et al. |
| 6,212,416 B1 | 4/2001 | Ward et al. |
| 6,299,604 B1 | 10/2001 | Ragheb et al. |
| 6,319,540 B1 | 11/2001 | Van Antwerp et al. |
| 6,475,750 B1 | 11/2002 | Han et al. |
| 6,497,729 B1 | 12/2002 | Moussy et al. |
| 6,565,509 B1 | 5/2003 | Say et al. |
| 6,565,960 B2 | 5/2003 | Koob et al. |
| 6,602,678 B2 | 8/2003 | Kwon et al. |
| 6,602,716 B1 | 8/2003 | Klimant |
| 6,642,015 B2 | 11/2003 | Vachon et al. |
| 6,671,527 B2 | 12/2003 | Petersson et al. |
| 6,702,857 B2 | 3/2004 | Brauker et al. |
| 6,750,311 B1 | 6/2004 | Van Antwerp et al. |
| 6,766,183 B2 | 7/2004 | Walsh et al. |
| 6,794,195 B2 | 9/2004 | Colvin, Jr. |
| 6,804,544 B2 | 10/2004 | Van Antwerp et al. |
| 6,818,226 B2 | 11/2004 | Reed et al. |
| 6,821,530 B2 | 11/2004 | Koob et al. |
| 6,844,023 B2 | 1/2005 | Schulman et al. |
| 6,965,791 B1 | 11/2005 | Hitchcock et al. |
| 6,994,691 B2 | 2/2006 | Ejlersen |
| 7,060,503 B2 | 6/2006 | Colvin, Jr. |
| 7,067,194 B2 | 6/2006 | Mao et al. |
| 7,110,803 B2 | 9/2006 | Shults et al. |
| 7,132,049 B2 | 11/2006 | Hou et al. |
| 7,134,999 B2 | 11/2006 | Brauker et al. |
| 7,153,265 B2 | 12/2006 | Vachon |
| 7,162,289 B2 | 1/2007 | Shah et al. |
| 7,186,789 B2 | 3/2007 | Hossainy et al. |
| 7,192,450 B2 | 3/2007 | Brauker et al. |
| 7,202,947 B2 | 4/2007 | Liu et al. |
| 7,226,978 B2 | 6/2007 | Tapsak et al. |
| 7,228,159 B2 | 6/2007 | Petersson et al. |
| 7,406,345 B2 | 7/2008 | Muller et al. |
| 7,424,317 B2 | 9/2008 | Parker et al. |
| 7,433,042 B1 | 10/2008 | Cavanaugh et al. |
| 7,450,980 B2 | 11/2008 | Kawanishi |
| 7,496,392 B2 | 2/2009 | Alarcon et al. |
| 7,541,598 B2 | 6/2009 | Aasmul |
| 7,567,347 B2 | 7/2009 | Aasmul |
| 7,653,424 B2 | 1/2010 | March |
| 7,772,286 B2 | 8/2010 | Muller et al. |
| 7,869,853 B1 | 1/2011 | Say et al. |
| 7,927,519 B2 | 4/2011 | Domschke et al. |
| 7,939,332 B2 | 5/2011 | Colvin, Jr. |
| 7,972,628 B2 | 7/2011 | Ratner et al. |
| 7,972,875 B2 | 7/2011 | Rogers et al. |
| 8,057,041 B2 | 11/2011 | Muller et al. |
| 8,131,333 B2 | 3/2012 | Chapoy et al. |
| 8,229,535 B2 | 7/2012 | Mensinger et al. |
| 8,235,897 B2 | 8/2012 | Gal et al. |
| 8,249,684 B2 | 8/2012 | Kamath et al. |
| 8,260,393 B2 | 9/2012 | Kamath et al. |
| 8,280,476 B2 | 10/2012 | Jina |
| 8,282,550 B2 | 10/2012 | Rasdal et al. |
| 8,318,193 B2 | 11/2012 | Ratner et al. |
| 8,343,092 B2 | 1/2013 | Rush et al. |
| 8,346,337 B2 | 1/2013 | Heller et al. |
| 8,346,363 B2 | 1/2013 | Darvish et al. |
| 8,368,556 B2 | 2/2013 | Sicurello et al. |
| 8,372,423 B2 | 2/2013 | Marshall et al. |
| 8,385,998 B2 | 2/2013 | Zhang et al. |
| 8,386,004 B2 | 2/2013 | Kamath et al. |
| 8,423,114 B2 | 4/2013 | Simpson et al. |
| 8,428,678 B2 | 4/2013 | Kamath et al. |
| 8,452,361 B2 | 5/2013 | Muller |
| 8,452,363 B2 | 5/2013 | Muller et al. |
| 8,460,231 B2 | 6/2013 | Brauker et al. |
| 8,465,425 B2 | 6/2013 | Heller et al. |
| 8,483,793 B2 | 7/2013 | Simpson et al. |
| 8,527,025 B1 | 9/2013 | Shults et al. |
| 8,527,026 B2 | 9/2013 | Shults et al. |
| 8,535,262 B2 | 9/2013 | Markle et al. |
| 8,543,182 B2 | 9/2013 | Botvinick et al. |
| 8,543,184 B2 | 9/2013 | Boock et al. |
| 8,543,354 B2 | 9/2013 | Luo et al. |
| 8,562,558 B2 | 10/2013 | Kamath et al. |
| 8,579,879 B2 | 11/2013 | Palerm et al. |
| 8,608,924 B2 | 12/2013 | Cooper et al. |
| RE44,695 E | 1/2014 | Simpson et al. |
| 8,622,903 B2 | 1/2014 | Jin et al. |
| 8,628,471 B2 | 1/2014 | Mazar et al. |
| 8,647,271 B2 | 2/2014 | Muller et al. |
| 8,647,393 B2 | 2/2014 | Marshall et al. |
| 8,666,471 B2 | 3/2014 | Rogers |
| 9,244,064 B2 | 1/2016 | Muller et al. |
| 9,826,926 B2 | 11/2017 | Muller et al. |
| 10,219,729 B2 | 3/2019 | Kintz et al. |
| 2002/0043651 A1 | 4/2002 | Darrow et al. |
| 2002/0048577 A1 | 4/2002 | Bornstein et al. |
| 2002/0094526 A1 | 7/2002 | Bayley et al. |
| 2002/0151772 A1 | 10/2002 | Polak |
| 2002/0193672 A1 | 12/2002 | Walsh et al. |
| 2003/0004554 A1 | 1/2003 | Riff et al. |
| 2003/0050542 A1 | 3/2003 | Reihl et al. |
| 2003/0088682 A1 | 5/2003 | Hlasny |
| 2003/0099682 A1 | 5/2003 | Moussy et al. |
| 2003/0171666 A1 | 9/2003 | Loeb et al. |
| 2003/0208166 A1 | 11/2003 | Schwartz |
| 2004/0106215 A1 | 6/2004 | Lehmann |
| 2004/0106951 A1 | 6/2004 | Edman et al. |
| 2004/0143221 A1 | 7/2004 | Shadduck |
| 2004/0176669 A1 | 9/2004 | Colvin, Jr. |
| 2004/0195528 A1 | 10/2004 | Reece et al. |
| 2004/0258732 A1 | 12/2004 | Shikinami |
| 2004/0259270 A1 | 12/2004 | Wolf |
| 2005/0027175 A1 | 2/2005 | Yang |
| 2005/0043606 A1 | 2/2005 | Pewzner et al. |
| 2005/0096587 A1 | 5/2005 | Santini, Jr. et al. |
| 2005/0118726 A1 | 6/2005 | Schultz et al. |
| 2005/0119737 A1 | 6/2005 | Bene et al. |
| 2005/0154374 A1 | 7/2005 | Hunter et al. |
| 2005/0182389 A1 | 8/2005 | LaPorte et al. |
| 2005/0245799 A1 | 11/2005 | Brauker et al. |
| 2006/0002890 A1 | 1/2006 | Hersel et al. |
| 2006/0002969 A1 | 1/2006 | Kyriakides et al. |
| 2006/0089548 A1 | 4/2006 | Hogan |
| 2006/0148983 A1 | 7/2006 | Muller et al. |
| 2006/0155179 A1 | 7/2006 | Muller et al. |
| 2006/0252976 A1 | 11/2006 | Rosero |
| 2006/0270919 A1 | 11/2006 | Brenner |
| 2006/0275340 A1 | 12/2006 | Udipi et al. |
| 2006/0289307 A1 | 12/2006 | Yu et al. |
| 2007/0002470 A1 | 1/2007 | Domschke et al. |
| 2007/0004046 A1 | 1/2007 | Abbott |
| 2007/0010702 A1 | 1/2007 | Wang et al. |
| 2007/0030443 A1 | 2/2007 | Chapoy et al. |
| 2007/0093617 A1 | 4/2007 | DesNoyer et al. |
| 2007/0105176 A1 | 5/2007 | Ibey et al. |
| 2007/0134290 A1 | 6/2007 | Rowland et al. |
| 2007/0135698 A1 | 6/2007 | Shah et al. |
| 2007/0244379 A1 | 10/2007 | Boock et al. |
| 2007/0270675 A1 | 11/2007 | Kane et al. |
| 2008/0020012 A1 | 1/2008 | Ju et al. |
| 2008/0139903 A1 | 6/2008 | Bruce et al. |
| 2008/0249381 A1 | 10/2008 | Muller et al. |
| 2009/0005663 A1 | 1/2009 | Parker et al. |
| 2009/0131773 A1 | 5/2009 | Struve et al. |
| 2009/0221891 A1 | 9/2009 | Yu et al. |
| 2009/0270953 A1 | 10/2009 | Ecker et al. |
| 2010/0113901 A1 | 5/2010 | Zhang et al. |
| 2010/0123121 A1 | 5/2010 | Taylor |
| 2010/0160749 A1 | 6/2010 | Gross et al. |
| 2010/0185066 A1 | 7/2010 | March |
| 2010/0202966 A1 | 8/2010 | Gross et al. |

(56) References Cited

U.S. PATENT DOCUMENTS

| | | |
|---|---|---|
| 2010/0249548 A1 | 9/2010 | Mueller |
| 2010/0303772 A1 | 12/2010 | McMillan et al. |
| 2011/0028806 A1 | 2/2011 | Merritt et al. |
| 2011/0036994 A1 | 2/2011 | Frayling |
| 2011/0215432 A1 | 9/2011 | Uematsu et al. |
| 2011/0224514 A1 | 9/2011 | Muller et al. |
| 2011/0230835 A1 | 9/2011 | Muller et al. |
| 2011/0306511 A1 | 12/2011 | Lea |
| 2012/0123276 A1 | 5/2012 | Govari et al. |
| 2012/0140094 A1 | 6/2012 | Shpunt et al. |
| 2012/0172686 A1 | 7/2012 | Esenaliev et al. |
| 2012/0172692 A1 | 7/2012 | Tamada et al. |
| 2012/0179014 A1 | 7/2012 | Shults et al. |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0226121 A1 | 9/2012 | Kamath et al. |
| 2012/0238852 A1 | 9/2012 | Brauker et al. |
| 2012/0245445 A1 | 9/2012 | Black et al. |
| 2012/0258551 A1 | 10/2012 | Herbrechtsmeier et al. |
| 2012/0265034 A1 | 10/2012 | Wisniewski et al. |
| 2012/0283538 A1 | 11/2012 | Rose et al. |
| 2012/0289796 A1 | 11/2012 | Esenaliev et al. |
| 2012/0296311 A1 | 11/2012 | Brauker et al. |
| 2013/0006069 A1 | 1/2013 | Gil et al. |
| 2013/0030273 A1 | 1/2013 | Tapsak et al. |
| 2013/0060105 A1 | 3/2013 | Shah et al. |
| 2013/0060106 A1 | 3/2013 | Aasmul et al. |
| 2013/0076531 A1 | 3/2013 | San Vicente et al. |
| 2013/0076532 A1 | 3/2013 | San Vicente et al. |
| 2013/0078912 A1 | 3/2013 | San Vicente et al. |
| 2013/0158413 A1 | 6/2013 | Lisogurski et al. |
| 2013/0211212 A1 | 8/2013 | Stumber |
| 2013/0211213 A1 | 8/2013 | Dehennis et al. |
| 2013/0213110 A1 | 8/2013 | Papadimitrakopoulos et al. |
| 2013/0229660 A1 | 9/2013 | Goldschmidt et al. |
| 2013/0231542 A1 | 9/2013 | Simpson et al. |
| 2013/0310666 A1 | 11/2013 | Shults et al. |
| 2013/0310670 A1 | 11/2013 | Boock et al. |
| 2013/0311103 A1 | 11/2013 | Cooper et al. |
| 2013/0337468 A1 | 12/2013 | Muller et al. |
| 2014/0000338 A1 | 1/2014 | Luo et al. |
| 2014/0275869 A1 | 9/2014 | Kintz et al. |
| 2014/0316224 A1 | 10/2014 | Sato |
| 2014/0357964 A1 | 12/2014 | Wisniewski et al. |
| 2014/0364707 A1 | 12/2014 | Kintz et al. |
| 2016/0213288 A1 | 7/2016 | Wisniewski et al. |
| 2016/0374556 A1 | 12/2016 | Colvin et al. |
| 2017/0087376 A1 | 3/2017 | McMillan et al. |
| 2017/0325722 A1 | 11/2017 | Wisniewski et al. |

FOREIGN PATENT DOCUMENTS

| | | |
|---|---|---|
| JP | S59-189828 A | 10/1984 |
| JP | H08-304741 A | 11/1996 |
| JP | H09-257440 A | 10/1997 |
| JP | 2001-508340 T | 6/2001 |
| JP | 2001-320034 A | 11/2001 |
| JP | 2003-054025 A | 2/2003 |
| JP | 2003-222640 A | 8/2003 |
| JP | 2004-267613 | 9/2004 |
| JP | 2004-537344 | 12/2004 |
| JP | 2006-051374 A | 2/2006 |
| JP | 2006-280934 | 10/2006 |
| JP | 2007-044512 A | 2/2007 |
| JP | 2008-523375 A | 7/2008 |
| JP | 2008-541881 | 11/2008 |
| JP | 2009-526993 | 7/2009 |
| JP | 2012-095803 A | 5/2012 |
| JP | 5076035 | 11/2012 |
| JP | 2013-103094 A | 5/2013 |
| JP | 2013-104851 A | 5/2013 |
| WO | WO 91/09312 | 6/1991 |
| WO | WO 97/19188 | 5/1997 |
| WO | WO 98/06406 | 2/1998 |
| WO | WO 2000/002048 | 1/2000 |
| WO | WO 2001/018543 | 3/2001 |
| WO | WO 2002/087610 | 11/2002 |
| WO | WO 2003/006992 | 1/2003 |
| WO | WO 2005/120631 | 12/2005 |
| WO | WO 2006/004595 | 1/2006 |
| WO | WO 2006/010604 | 2/2006 |
| WO | WO 2006/044972 | 4/2006 |
| WO | WO 2006/130461 | 12/2006 |
| WO | WO 2007/126444 | 11/2007 |
| WO | WO 2008/141241 | 11/2008 |
| WO | WO 2008/142158 | 11/2008 |
| WO | WO 2008/143651 | 11/2008 |
| WO | WO 2009/106805 | 9/2009 |
| WO | WO 2010/037847 | 4/2010 |
| WO | WO 2010/133831 | 11/2010 |
| WO | WO 2010/141377 | 12/2010 |
| WO | WO 2011/101624 | 8/2011 |
| WO | WO 2011/101625 | 8/2011 |
| WO | WO 2011/101627 | 8/2011 |
| WO | WO 2011/101628 | 8/2011 |
| WO | WO 2012/048150 | 4/2012 |
| WO | WO 2013/036493 | 3/2013 |
| WO | WO 2013/073270 | 5/2013 |
| WO | WO 2013/132400 | 9/2013 |
| WO | WO 2014/158988 | 10/2014 |
| WO | WO 2014/160258 | 10/2014 |

OTHER PUBLICATIONS

Examination Report for Canadian Application No. 2913474, dated Mar. 12, 2021, 6 pages.

Examination Report for Canadian Application No. 2913474, dated Dec. 8, 2021, 7 pages.

Decision of Rejection for Japanese Application No. 2016-518027, dated Feb. 12, 2019, 18 pages.

Extended European Search report for European Application No. 20176588.0, dated Dec. 11, 2020, 7 pages.

Office Action for Japanese Application No. 2019-109783, dated Feb. 13, 2020, 6 pages.

Office Action for Japanese Application No. 2019-109783, dated Feb. 9, 2021, 9 pages.

Office Action for Japanese Application No. 2019-109783, dated Dec. 6, 2021, 11 pages.

Office Action for U.S. Appl. No. 14/297,787, dated Oct. 6, 2017, 12 pages.

Office Action for U.S. Appl. No. 14/297,787, dated Jan. 26, 2017, 11 pages.

Office Action for U.S. Appl. No. 14/297,787, dated Jul. 8, 2016, 9 pages.

Examination Report No. 1 for Australian Application No. 2014274784, dated Jan. 29, 2018, 7 pages.

First Office Action for Chinese Application No. 201480031998.X, dated Jan. 8, 2018, 8 pages.

Supplementary European Search Report for European Application No. 14807637.5, dated Dec. 21, 2016, 7 pages.

Office Action for Japanese Application No. 2016-518027, dated Apr. 4, 2018, 16 pages.

International Search Report and Written Opinion for International Application No. PCT/US2014/041284, dated Dec. 4, 2014, 17 pages.

Alexeev et al., "High ionic strength glucose-sensing photonic crystal," Anal. Chem., 75:2316-2323 (2003).

Alexeev et al., "Photonic crystal glucose-sensing material for non-invasive monitoring of glucose in tear fluid," Clinical Chemistry, 50(12):2353-2360 (2004).

Aslan et al., "Nanogold plasmon-resonance-based glucose sensing 2: wavelengthratiometric resonance light scattering," Anal. Chem., 77(7):2007-2014 (2005).

Badylak et al., "Immune response to biologic scaffold materials," Seminars in Immunology, 20(2): 109-116 (2008).

(56) References Cited

OTHER PUBLICATIONS

Ballerstadt et al., "Competitive-binding assay method based on fluorescence quenching of ligands held in close proximity by a multivalent receptor," Anal. Chem., Acta. 345:203-212 (1997).
Bhardwaj, U. et al., "A review of the development of a vehicle for localized and controlled drug delivery for implantable biosensors," Journal of Diabetes Science and Technology, 2(6): 1016-1029 (2008).
Billingsley et al., "Fluorescent nano-optodes for glucose detection," Anal. Chem., 82(9):3707-3713 (2010).
Brasuel et al., "Fluorescent nanosensors for intracellular chemical analysis: decyl methacrylate liquid polymer matrix and ion-exchange-based potassium pebble sensors with real-time application to viable rat C6 glioma cells," Anal. Chem., 73(10):2221-2228 (2001).
Brasuel et al., "Liquid polymer nano-pebbles for CL- analysis and biological applications," Analyst, 128(10):1262-1267 (2003).
Braun et al., "Comparison of tumor and normal tissue oxygen tension measurements using oxylite or microelectrodes in rodents," Am. J. Physiol. Heart Circ. Physiol., 280(6):H2533-H2544 (2001).
Bridges et al., "Chronic inflammatory responses to microgel-based implant coatings," J Biomed. Mater. Res. A., 94(1):252-258 (2010).
Chaudhary et al., "Evaluation of glucose sensitive affinity binding assay entrapped in fluorescent dissolved-core alginate microspheres," Biotechnology and Bioengineering, 104(6):1075-1085 (2009).
Cordeiro, P.G. et al., "The protective effect of L-arginine on ischemia-reperfusion injury in rat skin flaps," Plast Reconstruct Surg., 100(5):1227-1233 (1997).
Dunphy, I. et al., "Oxyphor R2 and G2: phosphors for measuring oxygen by oxygen-dependent quenching phosphorescence," Anal. Biochem., 310:191-198 (2002).
Garg, S. K. et al., "Improved glucose excursions using an implantable real-time continuous glucose sensor in adults with Type 1 diabetes," Diabetes Care, 27(3)734-738 (2004).
Henninger, N., et al., "Tissue response to subcutaneous implantation of glucose-oxidase-based glucose sensors in rats," Biosens Bioelectron, 23(1):26-34 (2007).
Horgan et al., "Crosslinking of phenylboronic acid receptors as a means of glucose selective holographic detection," Biosensors and Bioelectronics, 21 (9):1838-1845 (2006).
Ibey et al., "Competitive binding assay for glucose based on glycodendrimer fluorophore conjugates," Anal. Chem., 77(21)7039-7046 (2005).
Isenhath et al., "A mouse model to evaluate the interface between skin and a percutaneous device," J Biomed. Mater. Research, 83A:915-922 (2007).
Ju, Y. M. et al., "A novel porous collagen scaffold around an implantable biosensor for improving biocompatibility. I. In vitrol in vivo stability of the scaffold and in vitro sensitivity of the glucose sensor with scaffold," J Biomed. Mater. Research, 87A:136-146 (2008), Available online Dec. 17, 2007.
Kaehr et al., "Multiphoton fabrication of chemically responsive protein hydrogels for microactuation," PNAS USA, 105(26):8850-8854 (2008).
Kasprzak, S. E., "Small-scale polymer structures enabled by thiol-ene copolymer systems," Doctoral Dissertation, Georgia Institute of Technology, May 2009, 170 pages.
Klimowicz, A. et al., "Evaluation of skin penetration of topically applied drugs by cutaneous microdialysis:acyclovir vs salicylic acid," J Clin Pharm Ther, 3(2):143-148 (2007).
Kloxin, A. M. et al., "Photodegradable hydrogels for dynamic tuning of physical and chemical properties," Science, 324:59-63 (2009).
Leavesley, S. J. et al., "Hyperspectral imaging microscopy for identification and quantitative analysis of fluorescently-labeled cells in highly autofluorescent tissue," J. Biophontonics, Jan. 2012; 5(1):67-84. doi: 10.1002/jbio.201100066. Epub Oct. 11, 2011.
Mansouri et al., "A miniature optical glucose sensor based on affinity binding," Nature Biotechnology, 23:885-890 (1984).
Marshall et al., "Biomaterials with tightly controlled pore size that promote vascular in-growth," ACS Polymer Preprints, 45(2):100-101 (2004).
McShane et al., "Glucose monitoring using implanted fluorescent microspheres," IEEE Engineering in Medicine and Biology Magazine, 19(6):36-45 (2000).
Nagler, A. et al., "Topical treatment of cutaneous chronic graft versus host disease with halofuginone: a novel inhibitor of collagen Type 1 synthesis," Transplantation, 68(11):1806-1809 (1999).
Nielsen et al., "Clinical evaluation of a transcutaneous interrogated fluorescence lifetime-based microsensor for continuous glucose reading," J Diabetes and Technology, 3(1):98-109 (2009).
Nielson, R. et al., "Microreplication and design of biological architectures using dynamicmask multiphoton lithography," Small, 5(1):120-125 (2009).
Onuki, Y. et al., "A review of the biocompatibility of implantable devices: Current challenges to overcome foreign body response," Journal of Diabetes Science and Technology, 2(6):1003-1015 (2008).
Ostendorf, A. et al., "Two-photon polymerization: a new approach to micromachining," Photonics Spectra, 40(10)72-79 (2006).
Ozdemir et al., "Axial pattern composite prefabrication of high-density porous polyethylene: experimental and clinical research," Plast. Reconstr. Surg., 115(1):183-196 (2005).
Phelps et al., "Bioartificial matrices for therapeutic vascularization," PNAS USA, 107(8):3323-3328 (2010).
Pickup, J. C. et al., "In vivo glucose monitoring: the clinical reality and the promise," Biosens Bioelectron., 20(10):1897-1902 (2005), Available online Oct. 3, 2004.
Rounds et al., "Microporated peg spheres for fluorescent analyte detection," Journal of Fluorescence, 17(1):57-63 (2007), Available online Nov. 17, 2006.
Russell et al., "A fluorescence-based glucose biosensor using concanavalin A and dextran encapsulated in apoly(ethylene glycol) hydrogel," Anal. Chem., 71(15):3126-3132 (1999).
Sanders et al., "Tissue response to single-polymer fibers of varying diameters: evaluation of fibrous encapsulation and macrophage density," J Biomed. Mater. Research, 52:231-237 (2000).
Sanders et al., "Tissue response to microfibers of different polymers: polyester, polyethylene, polylactic acid, and polyurethane," J Biomed. Mater. Research, 62(2):222-227 (2002).
Sanders et al., "Fibrous encapsulation of single polymer microfibers depends on their vertical dimension in subcutaneous tissue," J Biomed. Mater. Research, 67A:1181-1187 (2003).
Sanders et al., "Relative influence of polymer fiber diameter and surface charge on fibrous capsule thickness and vessel density for single-fiber implants," J Biomed. Mater. Research, 65A:462-467 (2003).
Sanders et al., "Polymer microfiber mechanical properties: a system for assessment and investigation of the link with fibrous capsule formation," J Biomed. Mater. Research, 67A:1412-1416 (2003).
Sanders et al., "Small fiber diameter fibro-porous meshes: tissue response sensitivity to fiber spacing," J Biomed Mater Research, 72A:335-342 (2005).
Sanders et al., "Fibro-porous meshes made from polyurethane micro-fibers: effects of surface charge on tissue response," Biomaterials, 26(7):813-818 (2005).
Schultz et al., "Affinity sensor: a new technique for developing implantable sensors for glucose and other metabolites," Diabetes Care, 5(3)245-253 (1982).
Shibata, H et al., "Injectable hydrogel microbeads for fluorescence-based in vivo continuous glucose monitoring", Proceedings of the National Academy of Sciences of the United States of America, Oct. 19, 2010, vol. 107, No. 42, p. 17894-17898.
Smith, J. L., "The Pursuit of Noninvasive Glucose: 'Hunting the Deceitful Turkey,'" (2006), 136 pages.
Srivastava et al., "Application of self-assembled ultrathin film coatings to stabilize macromolecule encapsulation in alginate microspheres," J of Microencapsulation, 22(4):397-411 (2005).
Srivastava et al., "Stabilization of glucose oxidase in alginate microspheres with photo reactive diazoresin nanofilm coatings," Biotechnology and Bioengineering, 91(1):124-131 (2005).

(56) References Cited

OTHER PUBLICATIONS

Takano et al., "An oxo-bacteriochlorin derivative for long-wavelength fluorescence ratiometric alcohol sensing," Analyst, 135:2334-2339 (2010).

Tian et al., "Dually fluorescent sensing of PH and dissolved oxygen using a membrane made from polymerizable sensing monomers," Sensors and Actuators B, 147:714-722 (2010).

Tian et al., "Influence of matrices on oxygen sensing of three-sensing films with chemically conjugated platinum porphyrin probes and preliminary application for monitoring of oxygen consumption of *escherichia coli* (e. coli)," Sensors and Actuators B, 150:579-587 (2010).

Tian, Y. et al., "A New Cross-linkable Oxygen Sensor Covalently Bonded into Poly(2-hydroxyethylmethacrylate)-co-Polyacrylamide Thin Film for Dissolved Oxygen Sensing," Chemistry Materials, 22(6):2069-2078 (2010).

Vidavalur, R. et al., "Sildenafil induces angiogenic response in human coronary arterioloar endothelial cells through the expression of thioredoxin, hemaoxygenase, and VEGF," Vasc Pharm, 45(2):91-95 (2006).

Ward, W. K. et.al., "The effect of microgeometry, implant thickness and polyurethane chemistry on the foreign body response to subcutaneous implants," Biomaterials, 23(21):4185-4192 (2002).

Wisniewski, N. et.al., "Characterization of implantable biosensor membrane fouling," Fresen J Anal Chem., 366 (6-7):611-621 (2000).

Wisniewski, N. et al., "Methods for reducing biosensor membrane biofouling," Colloids and Surfaces B: Biointerfaces, 18:197-219 (2000).

Woderer, S., "Continuous glucose monitoring in interstitial fluid using glucose oxidase-based sensor compared to established blood glucose measurement in rats," Anal Chim Acta., 581(1):7-12 (2007), Available online Aug. 18, 2006.

Young et al., "A novel porous collagen scaffold around an implantable biosensor for improving biocompatibility. I. In vitro/in vivo stability of the scaffold and in vitro sensitivity of the glucose sensor with scaffold," Journal of Biomedical Materials Research Part A., 2008, vol. 87, pp. 136-146.

\* cited by examiner

APPARATUS AND METHODS FOR DETECTING OPTICAL SIGNALS FROM IMPLANTED SENSORS

CROSS REFERENCE TO RELATED APPLICATIONS

This application is a continuation of U.S. patent application Ser. No. 14/297,787, entitled "Apparatus and Methods for Detecting Optical Signals From Implanted Sensors," filed Jun. 6, 2014, which claims priority under 35 U.S.C. § 119(e) to provisional U.S. patent application No. 61/832,065, entitled "Detection of Implant Optical Signals with Off-Axis Light Restriction," and to provisional U.S. patent application No. 61/832,078, entitled "Detection of Implant Optical Signals with Large Ratio of Surface Area," each filed Jun. 6, 2013, the disclosure of each of which is incorporated herein by reference in their entirety.

STATEMENT REGARDING FEDERALLY SPONSORED RESEARCH OR DEVELOPMENT

This invention was made with government support under grant numbers NIH R01 EB016414 and NIH R43 DK093139, awarded by the National Institutes of Health. The government has certain rights in the invention.

BACKGROUND

Some embodiments described herein relate to apparatus and methods for monitoring an implant, and in particular to apparatus and methods for detecting optical signals emitted from an implant with restriction of off-axis light.

Some embodiments described herein relate to apparatus and methods for monitoring an implant, and in particular to apparatus and methods for detecting optical signals through a relatively large surface area of tissue relative to a surface area of tissue through which an excitation optical signal is supplied.

The monitoring of the level or concentration of an analyte, such as glucose, lactate, oxygen, etc., in certain individuals is important to their health. High or low levels of glucose, or other analytes, may have detrimental effects or be indicative of specific health states. The monitoring of glucose is particularly important to persons with diabetes, a subset of whom must determine when insulin is needed to reduce glucose levels in their bodies or when additional glucose is needed to raise the level of glucose in their bodies.

A conventional technique used by many persons with diabetes for monitoring their blood glucose level includes the periodic drawing of blood, the application of that blood to a test strip, and the determination of the blood glucose level using calorimetric, electrochemical, or photometric detection. This technique does not permit continuous or automatic monitoring of glucose levels in the body, but typically must be performed manually on a periodic basis. Unfortunately, the consistency with which the level of glucose is checked varies widely among individuals. Many persons with diabetes find the periodic testing inconvenient, and they sometimes forget to test their glucose level or do not have time for a proper test. In addition, some individuals wish to avoid the pain associated with the test. Unmonitored glucose may result in hyperglycemic or hypoglycemic episodes. An implanted sensor that monitors the individual's analyte levels would enable individuals to monitor their glucose, or other analyte levels, more easily.

Some known devices perform in situ monitoring of analytes (e.g., glucose) in the blood stream or interstitial fluid of various tissues. A number of these devices use sensors that are inserted into a blood vessel or under the skin of a patient. Communicating and/or retrieving data from such known and/or proposed devices, however, can be challenging. For example, an implanted sensor may be able to communicate with a detector or receiver using radio frequency (RF) transmissions. Such a sensor, however, may require electronics, batteries, antennae, and/or other communication hardware which may increase the bulk of the implanted sensor, may require frequent inconvenient recharging, and/or may decrease the longevity or reliability of the implant.

A need therefore exists for apparatus and methods for detecting optical signals from an implanted sensor, such that a fluorescent sensor can be used. A fluorescent sensor may not require electric charging and/or transmission electronics. Such implanted sensors, however, may be difficult to read or to monitor optically because of low levels of florescence in the presence of high scatter due to dynamic changes in skin conditions (e.g., blood level and hydration). The skin is highly scattering, and the scattering may dominate the optical propagation. Scatter is caused by index of refraction changes in the tissue, and the main components of scatter in the skin are due to lipids, collagen, and other biological components. The main absorption is caused by blood, melanin, water, and other components.

Devices and apparatus described herein are suitable for providing accurate and consistent measurement of an analyte by monitoring an implantable sensor in such low-signal, high-scattering environments.

SUMMARY

Some embodiments described herein relate to an apparatus including a light source configured to transmit an excitation optical signal to an implanted sensor and a detector configured to detect an analyte-dependent optical signal emitted from an implanted sensor. The apparatus can include a lens configured to focus at least a portion of the analyte-dependent optical signal onto the detector.

Some embodiments described herein relate to an array of lenses. Each lens from the array of lenses can be configured to transmit an analyte-dependent optical signal from an implanted sensor to a detector. A plurality of light-blocking elements can be disposed within a substrate of the array of lenses. Each light blocking element from the array of light-blocking elements can be configured to prevent or inhibit a photon having an angle of incidence greater than a predetermined angle of incidence from passing through the substrate.

Some embodiments described herein relate to an apparatus including a detector configured to detect an analyte-dependent optical signal from an implanted sensor. A lens can be configured to focus at least a portion of the analyte-dependent optical signal onto the detector. A filter can be configured to attenuate light having wavelengths shorter than the analyte-dependent optical signal.

Some embodiments described herein relate to an implant capable of emitting, in response to excitation light in at least one excitation wavelength range, at least one analyte-dependent optical signal in at least one emission wavelength range. A device including at least one light source can be arranged to transmit the excitation light through tissue surrounding the implant. The device can include at least one detector arranged to detect light emitted from implanted sensor and transmitted through the tissue in the emission wavelength range. The device can also include an array of lenses arranged with an array of apertures to restrict transmission of off-axis light to the detector. The arrays of lenses and the array of apertures can be positioned with respect to the detector to restrict the light emitted from the tissue that travels to the detector based on the incidence angle of the emitted light. At least one layer of light control film can be arranged with the lens and aperture arrays to restrict the light emitted from the tissue that travels to the detector based on the incidence angle of the emitted light relative to the film. The device can further include at least one filter positioned to restrict transmission of light to the detector to wavelengths substantially within the emission wavelength range.

Some embodiments described herein relate to an optical detection device is for monitoring an implant embedded in tissue of a mammalian body. The implant is capable of emitting, in response to excitation light in at least one excitation wavelength range, at least one analyte-dependent optical signal in at least one emission wavelength range. The device can include at least one light source arranged to transmit the excitation light through the tissue to the implant. At least one detector is arranged to detect light emitted from the tissue in the emission wavelength range. The device can also include an array of lenses arranged with an array of apertures to restrict transmission of off-axis light to the detector. The arrays of lenses and the array of apertures are positioned with respect to the detector to restrict the light emitted from the tissue that travels to the detector according to an input angle of the emitted light. Light-blocking elements are arranged between the apertures to block propagation of incident light rays through the apertures. The light-blocking elements are positioned to block the incident light rays in accordance with an increase in incident angle of the light rays with respect to optical axes of the apertures. The device further comprises at least one filter arranged to restrict the transmission of the emitted light to the detector to wavelengths substantially within the emission wavelength range.

Some embodiments described herein relate to a method for monitoring an implant embedded in tissue of a mammalian body. The implant is capable of emitting, in response to excitation light in at least one excitation wavelength range, at least one analyte-dependent optical signal in at least one emission wavelength range. The method can include transmitting the excitation light through the tissue to the implant and detecting light emitted from the tissue in the emission wavelength range. The light in the emission wavelength range is transmitted through an array of lenses and an array of apertures arranged to restrict the light emitted from the tissue that travels to at least one detector according to an input angle of the emitted light. The light in the emission wavelength range is also transmitted through at least one layer of light control film arranged with the lens and aperture arrays to restrict the light emitted from the tissue that travels to the detector according to an incident angle of the emitted light relative to the film. The light in the emission wavelength range is also transmitted through at least one filter positioned to restrict transmission of light to the detector to wavelengths substantially within the emission wavelength range.

Some embodiments described herein relate to a method for monitoring an implant embedded in tissue of a mammalian body. The implant is capable of emitting, in response to excitation light in at least one excitation wavelength range, at least one analyte-dependent optical signal in at least one emission wavelength range. The method can include transmitting the excitation light through the tissue to the implant and detecting light emitted from the tissue in the emission wavelength range. An array of apertures arranged with an array of lenses restricts the light emitted from the tissue that travels to at least one detector according to an input angle of the emitted light. The method can also include blocking propagation of incident light rays through the apertures using light-blocking elements positioned between the apertures to block the incident light rays having an angle of incidence greater than a threshold angle of incidence based on, for example, the optical axes of the apertures. The method can further include filtering the emitted light to wavelengths substantially within the emission wavelength range.

Some embodiments described herein relate to an optical detection device for monitoring an implant embedded in tissue under skin. The implant is capable of emitting, in response to excitation light in at least one excitation wavelength range, at least one analyte-dependent optical signal in at least one emission wavelength range. The device can include at least one light source arranged to transmit the excitation light through a first surface area of the skin to the implant embedded in the tissue. One or more detectors can be arranged to detect light that is emitted from at least a second surface area of the skin, wherein the light source and one or more detectors are arranged such that the ratio of the surface area of the skin through which the detected light passes as it travels to the one or more detectors to the surface area of the skin through which the excitation light is transmitted is at least 4:1.

Some embodiments described herein relate to a method for monitoring an implant embedded in tissue under skin. The implant can be capable of emitting, in response to excitation light in at least one excitation wavelength range, at least one analyte-dependent optical signal in at least one emission wavelength range. The method can include transmitting the excitation light through a first surface area of the skin to the implant embedded in the tissue and detecting light that is emitted from at least a second surface area of the skin. The ratio of the surface area of the skin through which the detected light passes as it travels to one or more detectors to the surface area of the skin through which the excitation light is transmitted is at least 4:1.

DETAILED DESCRIPTION

Figure 1:
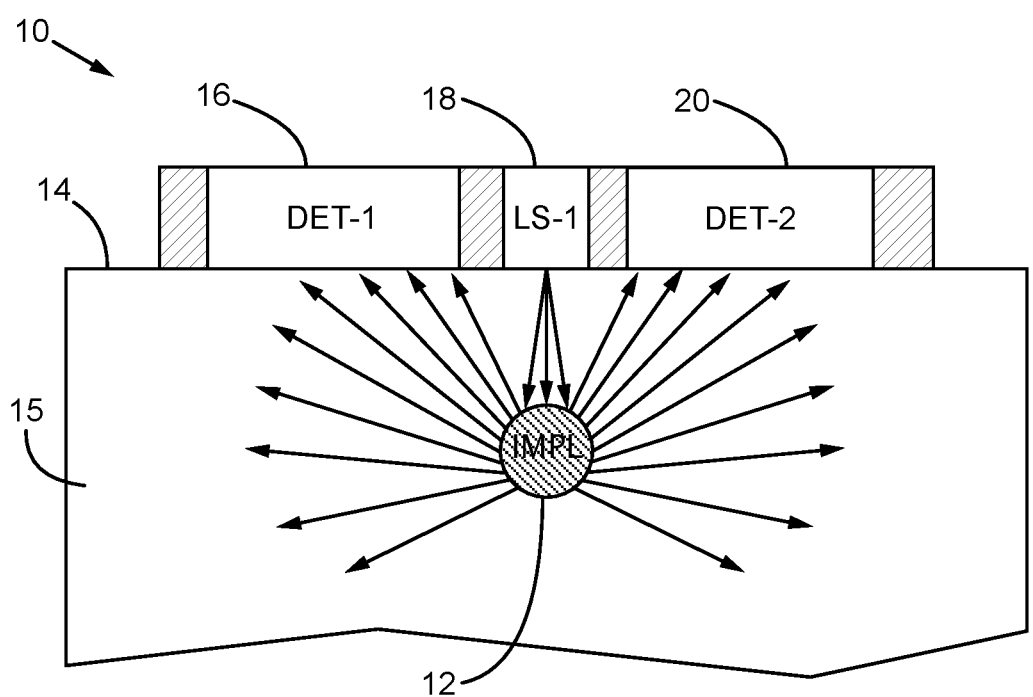
FIG. 1 is a schematic side view of an optical detection device for monitoring an implant, according to an embodiment.

According to some embodiments described herein, an optical detection device is provided for monitoring an implant embedded in tissue of a mammalian body. The implant can include a fluorophore-labeled target capable of emitting, in response to excitation light in at least one excitation wavelength range, at least one analyte-dependent optical signal in at least one emission wavelength range. The optical detection device can be operable to illuminate the implant with light whose wavelength content falls within an absorption band and/or collect light whose wavelength content is in an emission band.

The optical detection device can include excitation optics including a light source and/or optics operable to generate illumination in the absorption band. The optical detection device can also include emission optics operable to collect fluorescent emissions from the implant. Because in some instances, it may be difficult to obtain, design, and/or implement a light source that has a spectral content (i.e., wavelength range) that exactly matches every fluorophore absorption band, an optical filter or filters (usually band-pass filters) can be used along with the light source to limit the range of illuminating wavelengths to that of the absorption band and/or to reduce illuminating wavelengths of the emission band. Similarly, the emission optics can include another filter or filters operable to allow substantially only light with wavelengths in the emission band to reach the detector and/or to attenuate light with other wavelengths (e.g., light in the absorption band). Similarly stated, the optical detection device can include an optical system design operable to allow substantially only photons with wavelengths in the absorption band reach the target, and substantially only photons with wavelengths in the emission band reach the detector. Without proper optics, photons from the light source may be reach the detector and induce a measurement error.

Properly designing an optical system for an optical detection device can be complicated in instances in which the amount of emitted fluorescence to be detected is much less than the amount of excitation light scattered (e.g., not absorbed) by an intermediate surface (e.g., skin or tissue disposed between the optical detection device and the implant). One challenge is that the amount of excitation light that reaches the implant may be low because of the absorption and scattering caused by the various body parts (skin, tissue, etc.). The low amount of emitted fluorescence is further reduced by absorption and scattering as it makes its way out of the body towards the detector. Existing optical filter technology, which may provide rejection of unwanted photons on the order of (10') may be insufficient in these situations. Another challenge is that the difference between excitation and detection wavelengths (e.g., Stokes shift) may be quite small. A further challenge is that dichroic filters cause shifting (e.g., the "blue shift") of filter wavelengths as a function of the angle of light rays transmitted through the filter. Because of these challenges, standard fluorescence methods would allow through high background levels and, in turn, result in low Signal-to-Background (SBR) and Signal-to-Noise (SNR) ratios.

Some embodiments described herein relate to a compact device that can accurately and consistently monitor an implanted sensor. Such a device can be worn by a user substantially continuously and/or may not substantially restrict movements or activities of the user. The device and the sensor can collectively allow for continuous and/or automatic monitoring of an analyte and can provide a warning to the person when the level of the analyte is at or near a threshold level. For example, if glucose is the analyte, then the monitoring device might be configured to warn the person of current or impending hyperglycemia or hypoglycemia. The person can then take appropriate actions.

In the description contained herein, it is understood that all recited connections between structures can be direct operative connections or indirect operative connections through intermediary structures. A set of elements includes one or more elements. Any recitation of an element is understood to refer to at least one element. A plurality of elements includes at least two elements. Unless clearly indicated otherwise, any described method steps need not be necessarily performed in a particular or illustrated order. A first element (e.g. data) derived from a second element encompasses a first element equal to the second element, as well as a first element generated by processing the second element and optionally other data. Making a determination or decision according to a parameter encompasses making the determination or decision according to the parameter and optionally according to other data. Unless otherwise specified, an indicator of some quantity/data may be the quantity/data itself, or an indicator different from the quantity/data itself. Some embodiments described herein reference a wavelength, such as an excitation wavelength or an emission wavelength. Unless clearly indicated otherwise, a wavelength should be understood as describing a band of wavelengths including the wavelength. Computer programs described in some embodiments of the present invention may be stand-alone software entities or sub-entities (e.g., subroutines, code objects) of other computer programs. Computer readable media encompass non-transitory media such as magnetic, optic, and semiconductor storage media (e.g. hard drives, optical disks, flash memory, DRAM), as well as communications links such as conductive cables and fiber optic links. According to some embodiments, the present invention provides, inter alia, computer systems comprising hardware (e.g. one or more processors and associated memory) programmed to perform the methods described herein, as well as computer-readable media encoding instructions to perform the methods described herein.

The following description illustrates embodiments of the invention by way of example and not necessarily by way of limitation.

FIG. 1 is a schematic side view of an optical detection device 10 for monitoring an implanted sensor or implant 12, according to an embodiment. The implant 12 is embedded in tissue 15 of a mammalian body (which may be a piece of tissue that is attached or unattached to the rest of the body in various embodiments). The implant 12 can be embedded under a surface of skin 14. The implant 12 can be embedded and/or positioned in the subcutaneous tissue (e.g., in the range of 1 to 4 mm under the surface of the skin 14). The implant 12 is capable of emitting, in response to excitation light within an excitation wavelength range, at least one analyte-dependent optical signal within an emission wavelength range. The analyte may be, for example, glucose or other analytes in the tissue 15. Suitable optical signals include, without limitation, luminescent, bioluminescent, phosphorescent, autoluminescence, and diffuse reflectance signals. In some embodiments, the implant 12 contains one or more luminescent dyes (e.g., fluorescent dyes) whose luminescence emission intensity varies in dependence upon the amount or presence of target analyte in the body of the individual (e.g., in tissue 15).

A light source 18 is arranged to transmit excitation light within the excitation wavelength range from the surface of the skin 14, through the tissue 15, and to the implant 12. Suitable light sources include, without limitation, lasers, semi-conductor lasers, light emitting diodes (LEDs), and organic LEDs. Detectors 16, 20 are arranged with the light source 18 to detect light emitted from the tissue in the emission wavelength range. Suitable detectors include, without limitation, photodiodes, complementary metal-oxide-semiconductor (CMOS) detectors or charge-coupled device (CCD) detectors. Although multiple detectors are shown, a single and/or universal detector can be used.

The detectors can be 16, 20 filtered (e.g., with dichroic filters or other suitable filters) to measure the optical signals emitted within the wavelength ranges. For example, a suitable luminescent dye sensitive to glucose concentration is Alexa Flour® 647 responsive to excitation light (absorption) in the range of about 600 to 650 nm (absorption peak 647 nm) and within an emission wavelength range of about 670 to 750 nm with an emission peak of about 680 nm. Thus, in an embodiment in which the sensor includes Alexa Flour® 647, the detectors 16, 20 can be filtered from light having a wavelength shorter than about 650 nm or shorter than about 670 nm.

In some embodiments, the implant 12 is further capable of emitting, in response to excitation light within a second excitation wavelength range, at least one analyte-independent optical signal within a second emission wavelength range. For example, the implant 12 can contain an analyte-independent luminescence dye that functions to control for non-analyte physical or chemical effects on a reporter dye (e.g., photo bleaching or pH). Multiple dyes may be used. The analyte-independent optical signal is not modulated by analyte present in the tissue 15 and provides data for normalization, offset corrections, or internal calibration. The analyte-independent signal may compensate for non-analyte affects that are chemical or physiological (e.g., oxygen, pH, redox conditions) or optical (e.g., water, light absorbing/scattering compounds, hemoglobin). Alternatively, the analyte-independent signal may be provided by a stable reference dye in the implant 12. Suitable stable reference materials include, but are not limited to, lanthanide-doped crystals, lanthanide-doped nanoparticles, quantum dots, chelated lanthanide dyes, and metal (e.g., gold or silver) nanoparticles. The stable reference dye may provide a reference signal for other signals (e.g., to determine photo bleaching).

In the operation of device 10, the light source 18 is activated to transmit excitation light within the excitation wavelength range from the surface of the skin 14, through the tissue 15, and to the implant 12. The dye in the implant 12 absorbs some of the excitation light and emits fluorescence that depends on glucose or other analyte properties. The light may be emitted from the implant 12 in all directions, and scattered by the tissue 15. Some of the light that is emitted from the implant 12 is transmitted through the tissue 15 and detected by at least one of the detectors 16, 20. This can provide the primary analyte-dependent optical signal. In embodiments in which a reference optical signal is used for normalization, the light source 18 (or a second light source) is activated to transmit second excitation light from the surface of the skin 14 to the implant 12. At least one of the detectors 16, 20 measures, in response to the second excitation light, a second optical signal emitted from the tissue 15 through the surface of the skin 14.

The second optical signal may be used to normalize the primary analyte-dependent optical signal for scattering of light emitted from the implant 12. At least one corrected signal value may be calculated in dependence upon the measured optical signals. In one example, the primary analyte-dependent signal from the implant may be normalized by the analyte-independent optical signal emitted from the implant 12. Prior to executing optical reads for the analyte-dependent signal and/or the analyte-independent signal, a dark reading may be taken to account for background or ambient light, and this reading may be used to further correct the signals, e.g., by background subtraction.

In some embodiments, an analyte value (e.g., glucose concentration) is determined from the analyte-dependent signal and/or a ratio of multiple optical signals including one or more reference signals. In one example, the signal from the glucose sensitive fluorophore (e.g., Alexa Flour® 647) is normalized by the signal from a glucose insensitive fluorophore (e.g., Alexa Flour® 700). One suitable dye for the analyte-independent signal is Alexa Flour® 750 which is responsive to excitation light within an excitation wavelength range of about 700 to 760 nm (excitation peak 750 nm) and has an emission wavelength range of about 770 to 850 nm with an emission peak of about 780 nm.

An analyte value can be determined based on the optical signal(s) using, for example, a look-up table or calibration curve. Determining the analyte value can be implemented in software (executing on a processor) and/or hardware. For example, the optical device 10 can include a microprocessor. In some embodiments, the microprocessor is programmed to store measured optical signal values in a memory and/or to calculate normalized signal values and analyte concentrations. Alternatively, these functions may be performed in a separate processor or external computer in communication with the optical device 10. The external processor or computer can receive data representative of the measured optical signals and calculates the corrected signal value and analyte concentration. Alternatively, multiple processors may be provided, e.g., providing one or more processors in the optical device that communicate (wirelessly or with wires) with one or more external processors or computers.

In some embodiments in which two implant dyes (e.g., luminescent dyes) are utilized, it is possible that the implant dyes may share or overlap excitation (absorption) or emission wavelength ranges. In one example, the emission wavelength range of the first dye, which provides the analyte-dependent luminescence signal, shares or overlaps the excitation wavelength range of the second dye, which provides the analyte-independent luminescence signal. In another embodiment, the first and second dyes may share or overlap excitation wavelength ranges (so that a common light source may be used) and emit optical signals within different emission wavelength ranges. In another embodiment, the first and second dyes may be excited by light within different excitation wavelength ranges and emit optical signals within the same or overlapping emission wavelength range(s).

The implant 12 can be embedded in subcutaneous tissue (e.g., 1 to 4 mm under the surface of the skin 14). In some embodiments, the implant 12 comprises hydrogel scaffolds embedded with glucose-sensing nanospheres. The design of the implant 12 can use injectable, tissue-integrating, vascularizing scaffolds as the sensor. Embedded nanospheres emit luminescence that changes intensity and lifetime in response to the presence or concentration of the analyte (e.g., interstitial glucose). The spacing distances between each of the detectors 16, 20 and the light source 18 determine the depths of the respective light paths for detecting optical signals from the implant 12. The combination of an excitation light source and a detection band is an optical channel. The light source 18 and detectors 16, 20 can be arranged such that a surface area of skin 14 through which the excitation light is transmitted is located between substantially surrounding surface areas of skin 14 through which the detected light passes as it travels from the tissue 15 to one or more detectors 16, 20.

Although only one light source 18 and two detectors 16, 20 are shown in FIG. 1, in some embodiments, the optical device 10 can have any number of light sources and any number of detectors. The optical device 10 can have multiple possible combinations of spacing distances between multiple light sources and detectors. Such a multiple light source and/or multiple detector implementation can allow increased flexibility of the optical device 10. For example, since the depth of the implant 12 may be application-specific, an optical device 10 having multiple light sources and/or multiple detectors can be used for multiple applications.

The optical device 10 can be configured to ensure that substantially only photons with wavelengths in the excitation wavelength range(s) reach the implant 12, and substantially only photons with wavelengths in the emission wavelength ranges(s) reach at least one of the detectors 16, 20. Such an arraignment can minimize photons from the light source 18 reaching the detectors 16, 20, which can result in measurement error.

Figure 2:
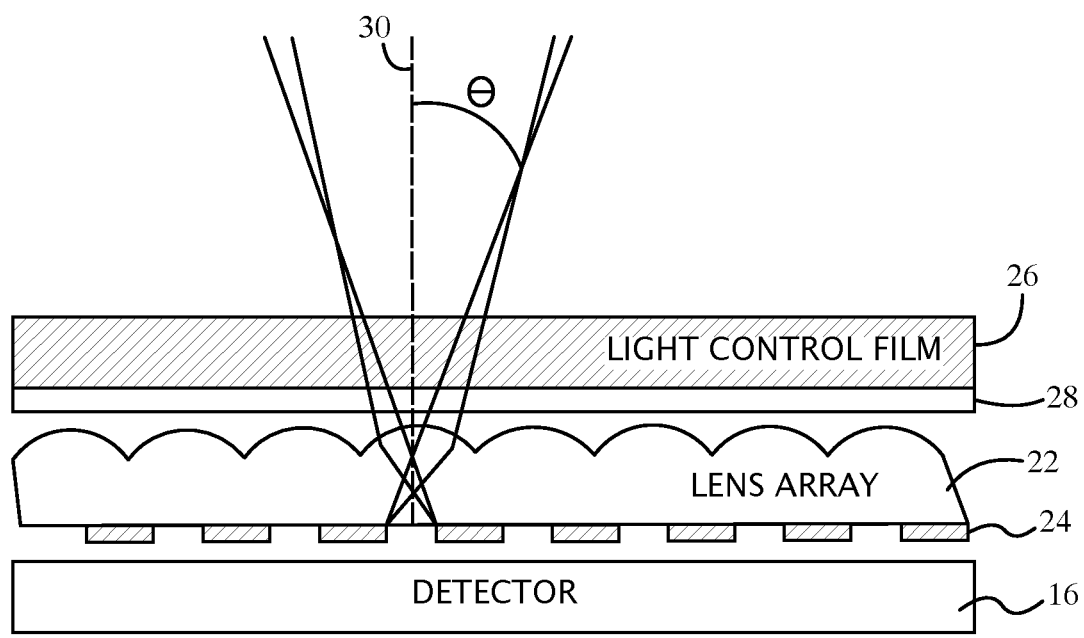
FIG. 2 is a schematic side view of an optical detection device for monitoring an implant, according to an embodiment.

FIG. 2 is a schematic side view of an optical detection device for monitoring an implant, according to an embodiment. An array of lenses 22 is aligned with an array of apertures 24 to restrict transmission of off-axis light to the detector 16. The lens arrays 22 and the aperture array 24 are positioned with respect to the detector 16 to collectively restrict the light emitted from the tissue that travels to the detector 16 based on an input angle θ (also referred to herein as incident angle) of the emitted light relative to optical axes 30 of the apertures. The optical axes 30 of the apertures can be substantially perpendicular to the surface of the detector 16. Each aperture from the array of apertures 24 can be substantially aligned with a lens from the array of lenses 22. Similarly stated the optical axes 30 of the apertures can be substantially coaxial with the center and/or axes of the lenses. For example, a substantially opaque portion of the array of apertures 24 can be positioned below the edges of the lenses.

At least one layer of light control film 26 is arranged with the lens array 22 and the aperture array 24. The light control film 26 can restrict the light emitted from the tissue from entering the lens array 22 and/or the aperture array 24 based on the incident angle of the emitted light relative to the film 26. In one example, the light control film 26 is Vikuti™ optical grade micro-louver privacy film commercially available from 3M™, which can block light having an incident angle greater than desired (e.g., greater than 24 degrees) relative to a perpendicular line through the film 26. This privacy film comprises a set of microlouvers that prevent light from large incident angles from reaching the lens array 22. In other embodiments, the film 26 comprises alternating transparent and opaque layers in an arrangement which is similar to a Venetian blind. Light propagating from angles greater than a desired incident angle can be absorbed and/or reflected.

At least one filter 28 (e.g., a dichroic or dielectric filter) is positioned to restrict transmission of light to the detector 16 to wavelengths substantially within the desired emission wavelength range. Because the detection of optical signals is dominated by low levels of return signals relative to the excitation light, the filter 28 can prevent scattered excitation light from blinding the detector 16. Suitable filters include band-pass, low-pass, and high pass filters depending upon the desired emission wavelength range for an application. Some modern optical filters have demonstrated $10^{-9}$ light rejection due to improvements in coating technologies. Additionally, intermediate layers of the optical detection system (e.g., the lens array 22, the aperture array 24, etc.) can include anti-reflective coatings to reduce or prevent light leaking through to the detector 16.

Due to fundamental properties of dichroic filters, maintaining a high level of light rejection requires careful design. One property of dichroic filters that detracts from light rejection is the "blue shift" as a function of input angle, where the transmittance wavelengths of dichroic filters change as a function of input angle. For the detection light emitted from the implant, there is a trade off between the input angle and the absolute optical signal. The light leaving the tissue is highly scattered and may form a lambertian distribution by the time it reaches the surface of the skin. The collection efficiency of the emitted light is proportional to ~$NA^2$, where NA=Numerical Aperture=n sin θ, and θ is the input angle. To improve the collection efficiency, the allowable input angle θ can be increased without increasing the angle so much to allow excitation light though the filter 28.

The lens array 22 and the aperture array 24 control the input angle θ of light traveling to the detector 16. The lens array 22 and an aperture array 24 restrict the light to an input angle less than θ, which in some embodiments is selected to be +/−20 degrees. The input angle θ can be controlled by varying the size of the apertures and the focal length of the micro lenses in the lens array 22. The smaller the aperture, then the smaller is input angle θ. The longer the focal length, then the smaller is input angle θ. Although not shown, a spacer can be used to maintain separation between the surface of the aperture array 24 and the lens array 22.

Figure 3:
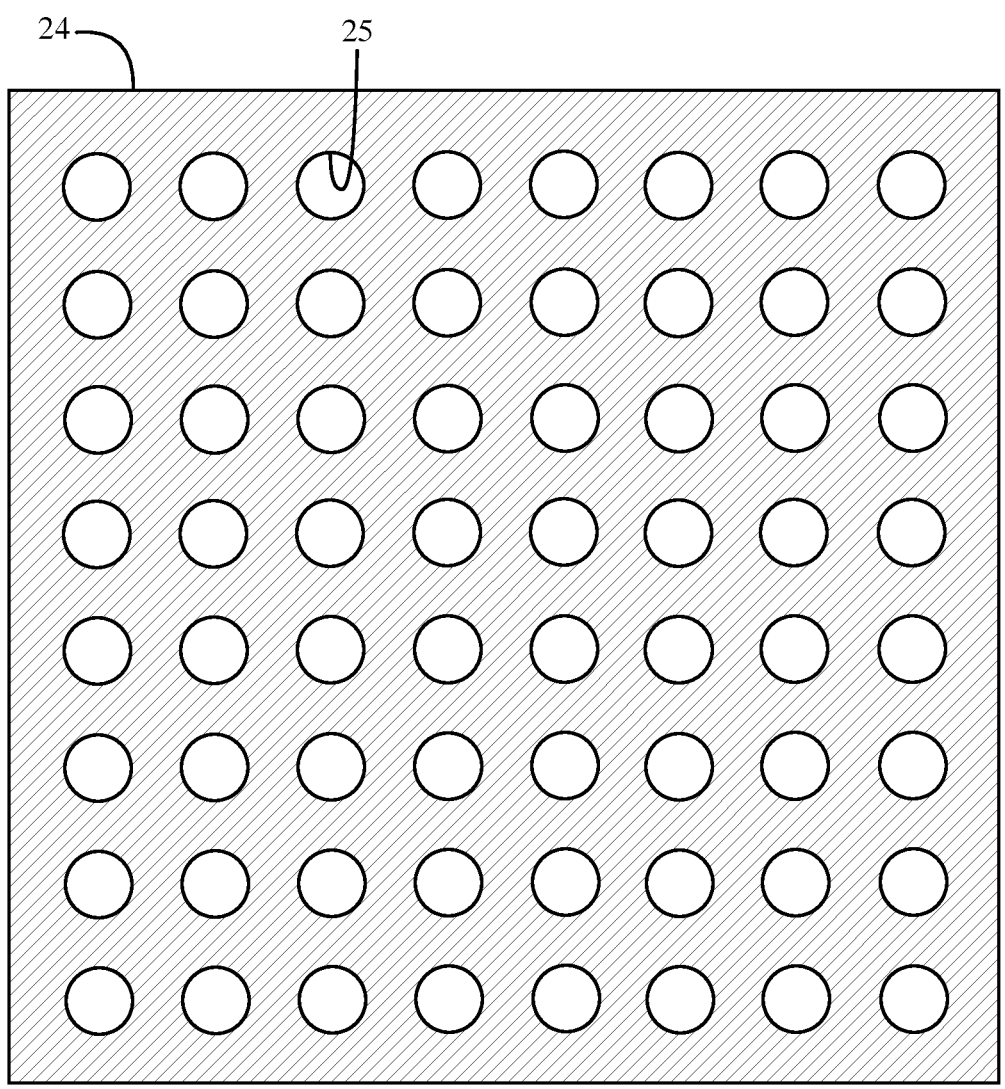
FIG. 3 is a plan view of an aperture array, according to an embodiment.

FIG. 3 is a plan view of the aperture array 24 having a plurality of apertures 25. In some embodiments, the aperture array 24 is constructed by patterning a metal mask on the surface of a silicon detector, such as the detector 16 shown in FIG. 2. The lens array 22 may be fabricated as etched glass or molded plastic. In some embodiments, the lens array 22 is a custom micro-lens array commercially available from JENOPTIK Optical Systems.

Figure 4:
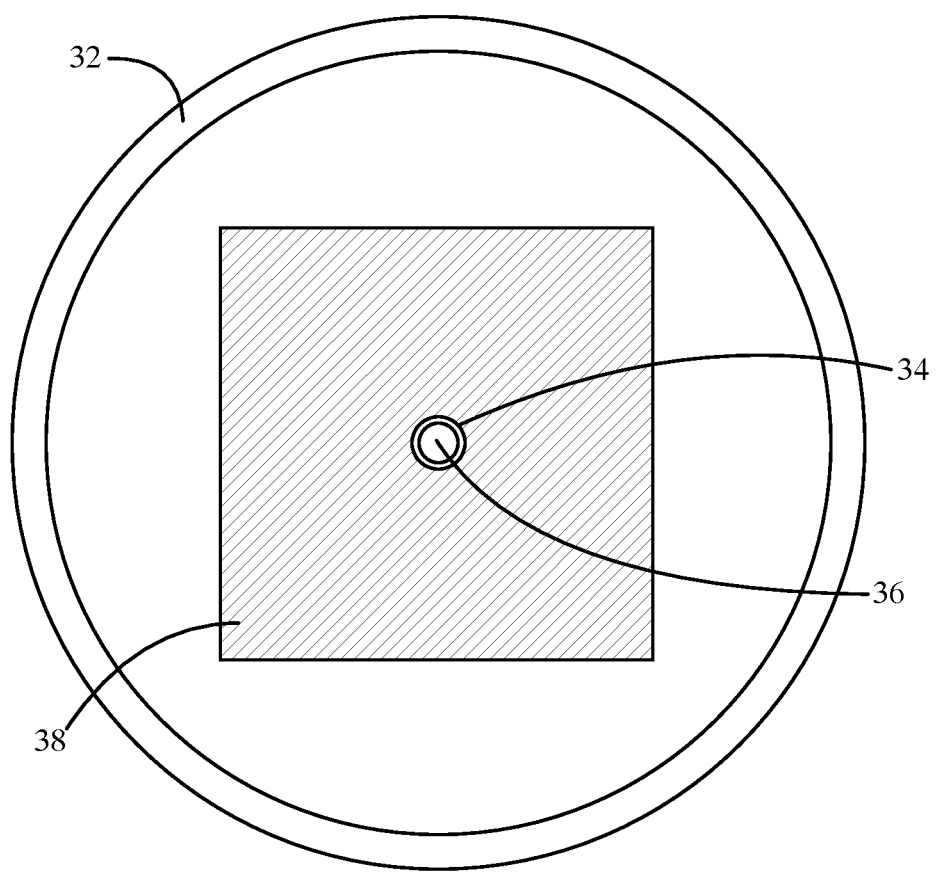
FIG. 4 is a schematic plan view of an optical detection device, according to an embodiment.

FIG. 4 is a schematic plan view of an optical detection device, according to an embodiment. The optical detection device of FIG. 4 is configured as a patch 32. At least one light source (not shown in FIG. 4) and detector 38 are arranged in an optical reader, such that the patch 32, that is configured to be placed on the skin. A light source is arranged to transmit the excitation light through a central via 34 in the patch 32, and a single universal detector 38 substantially surrounds the central via 34. In other embodiments, instead of the single detector 38, a plurality of detectors can be used, for example, substantially encircling the central via 34 to detect the emitted light in a plurality of emission wavelength ranges. In some embodiments, the optical detection device includes at least one light guiding component 36 in the central via 34. The light guiding component 36, such as a waveguide or optical fiber, is arranged to guide the excitation light to the skin. In some embodiments, a plurality of light sources (not shown for clarity in FIG. 4) are arranged to transmit the excitation light through the central via 34 (e.g., by means of one or more waveguides or optical fibers) in a plurality of different excitation wavelength ranges.

As one possible example, one or more light sources may be arranged to transmit excitation light to the skin through the central via 34 having a circular cross-section to transmit the excitation light through a substantially circular surface area of the skin having a diameter of about 1 mm and a corresponding excitation surface area of about 0.8 mm$^2$. The detector 38 has a square cross-section and is positioned to detect light emitted from a substantially square surface area of the skin through which the detected light passes as it travels to the detector 38. The detection surface area is substantially square with sides of 10 mm length, so that the total detection surface area is (10 mm×10 mm)−1 mm$^2$=99 mm$^2$. Accordingly, in this example, the ratio of detection surface area to excitation surface area is greater than 120:1.

Figure 5:
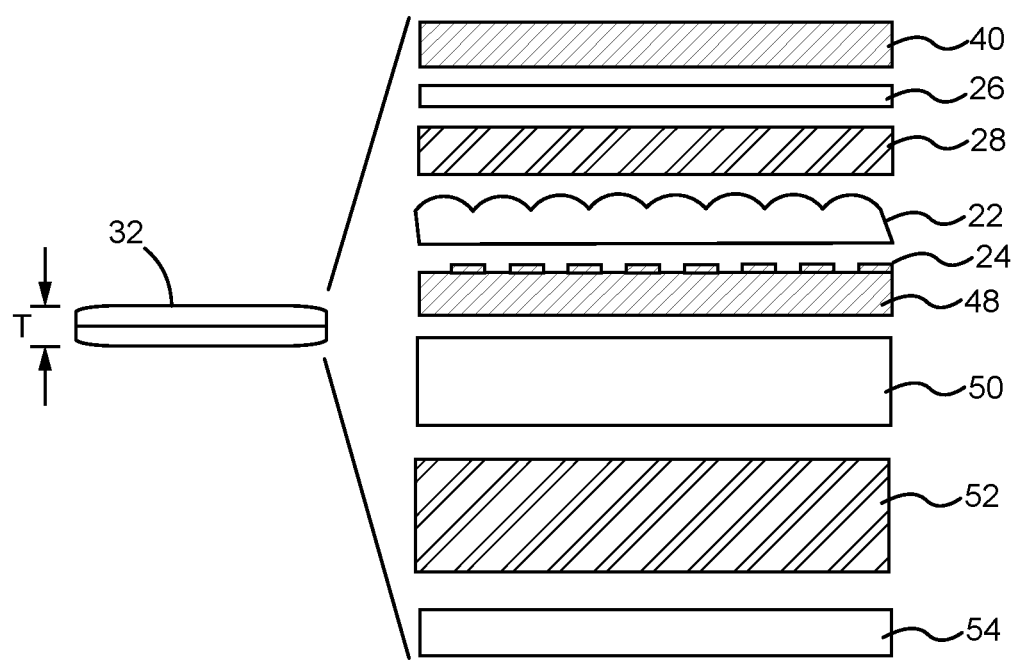
FIG. 5 is a schematic exploded view of an optical detection device, according to an embodiment.

FIG. 5 is a schematic exploded view of the patch 32. The patch 32 includes multiple layers. Dimensions of the patch 32 may be, for example, a diameter of about 16 mm and a thickness T of about 1.6 mm. In some embodiments, the layers may include a plastic cover 40 having a thickness of about 200 um, the light control film 26 having a thickness of about 100 um, the filter 28 having a thickness of about 200 um, the lens array 22 having a thickness of about 100 um, and the aperture array 24 patterned on a silicon detector layer 48 having a thickness of about 200 um. The layers can also include a printed circuit board (PCB) 50 having a thickness of about 400 um, a battery 52 having a thickness of about 300 um, and a case 54 having a thickness of about 200 um. The PCB 50 can include one or more light sources. The PCB 50 can also include processing electronics and/or a microprocessor in communication with one or more detectors in the detector layer 48 to receive data representative of the light detected in the emission wavelength range and programmed to determine at least one analyte value in dependence upon the data. The central via 34 may be formed through a stack of the layers (e.g., etched or drilled through the stack in the assembly process).

Figure 6:
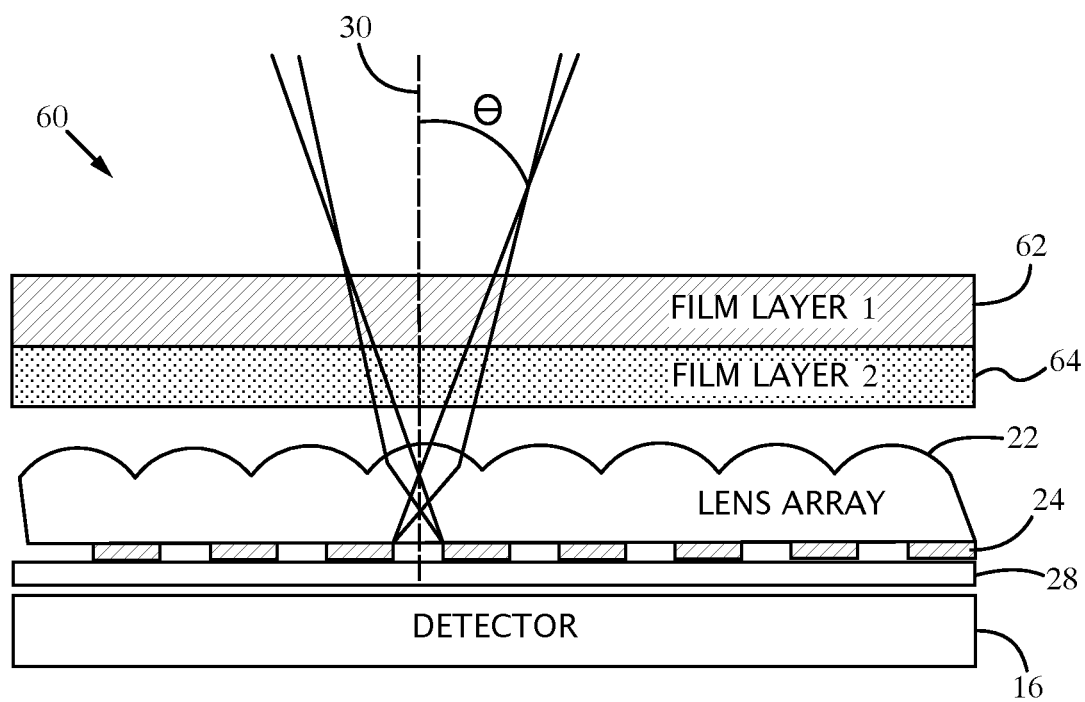
FIG. 6 is a schematic side view of an optical detection device for monitoring an implant, according to an embodiment.

FIG. 6 is a schematic side view of an optical detection device for monitoring an implant showing an arrangement of detection optics 60, according to an embodiment. In this embodiment, light emitted from the implant and tissue in the emission wavelength range is transmitted through at least two layers of light control films 62, 64. The two layers of light control films 62, 64 can restrict the light emitted from the tissue from entering the lens array 22 and/or the aperture array 24 based on the incident angle of the emitted light relative to the films 62, 64. In one example, the light control film 62 comprises alternating transparent and opaque layers in an arrangement which is similar to a Venetian blind. Light propagating from angles greater than a desired incident angle is absorbed. The light control film 64 may include Vikuti™ optical grade micro-louver privacy film commercially available from 3M™, which blocks light having an incident angle greater than desired (e.g., greater than 24 degrees) relative to a perpendicular line through the film 64.

In some embodiments, the light control film 62 and/or 64 may be operable to restrict light emitted from the tissue from entering the lens array 22 and the aperture array 24 based on a combination of incident angle and azimuth. For example, in an embodiment where the light control film 62 and/or 64 includes multiple micro-louvers, the light control film 62 and/or 64 may be effective at blocking high angle-of-incidence light having an azimuth substantially perpendicular to the micro-louvers, but may be relatively ineffective at blocking high angle-of-incidence light having an azimuth substantially parallel to the micro-louvers. In some such embodiments, two layers of light control film 62, 64 can be cross-hatched or otherwise disposed such that louvers or other light control elements are non-parallel such that the light control film 62, 64 are collectively effective at blocking high angle-of-incidence light having different azimuths.

In some embodiments, the films 62, 64 may be substantially the same as each other, or comprises different types of privacy film. Additionally, the filter 28 (e.g., a dichroic or dielectric filter) may be positioned between the aperture array 24 and the detector 16 to restrict the transmission of the emitted light to the detector 16 to wavelengths substantially within the emission wavelength range(s). The operation of the embodiment of FIG. 6 can be similar to the operation of the embodiment of FIGS. 1-2 previously described.

Figure 7:
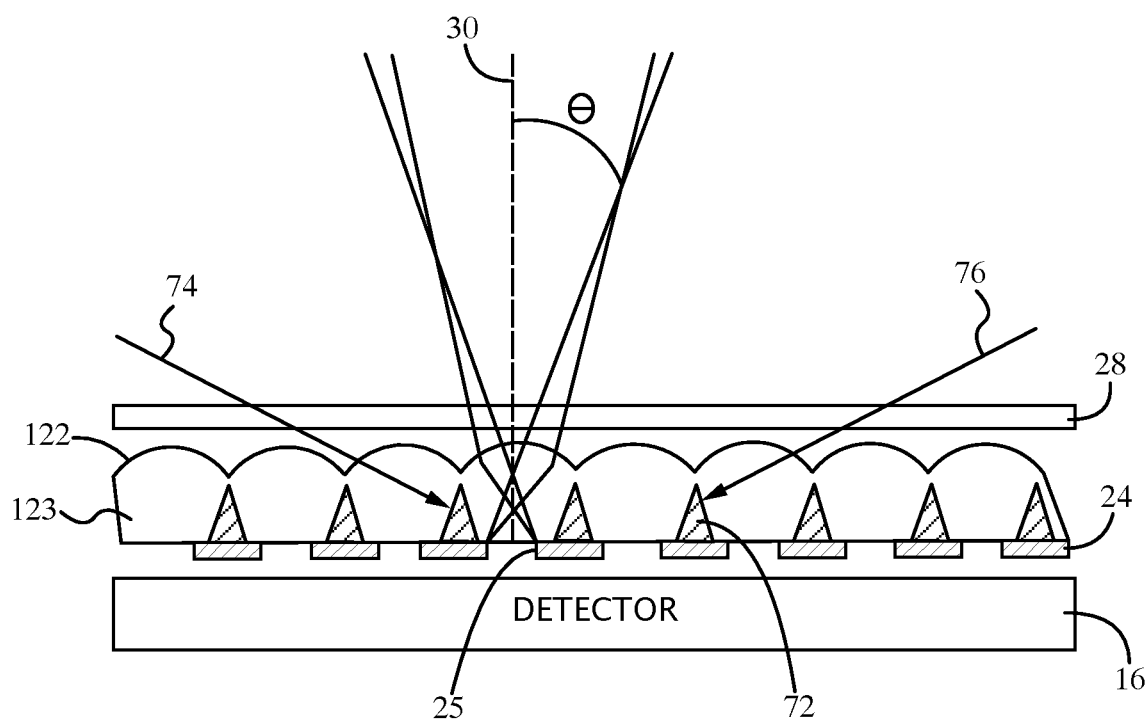
FIG. 7 is a schematic side view of an optical detection device for monitoring an implant, according to an embodiment.

FIG. 7 is a schematic side view of an optical detection device for monitoring an implant. An array of lenses 122 is aligned with an array of apertures 24 to restrict the transmission of off-axis light to the detector 16. The lens arrays 122 and the aperture array 24 are positioned with respect to the detector 16 to restrict the light emitted from the tissue that travels to the detector 16 according to an input angle θ of the emitted light relative to optical axis 30 of the apertures. The optical axis 30 of the apertures can be substantially perpendicular to the surface of the detector 16.

The lens array 122 includes light-blocking elements 72. The light-blocking elements 72 can be disposed between the apertures 25 to block propagation of off-axis light rays 74, 76 through the apertures 25. The light-blocking elements 72 can include black resin, metal, and/or metal film deposited in cavities of a substrate 123 of the lens array 122 positioned. At least one filter 28 is positioned to restrict the transmission of the emitted light to the detector 16 to wavelengths substantially within the emission wavelength range. Optionally, one or more layers of light control film may be included in this embodiment. The operation of the embodiment of FIG. 7 can be similar to the operation of the embodiment of FIGS. 1-2 previously described.

Figure 8A:
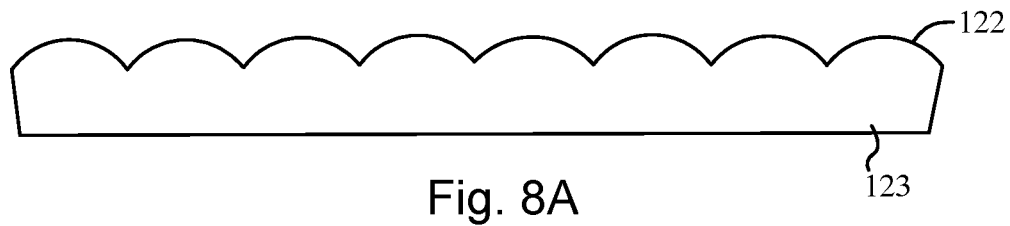
FIGS. 8A-8D depict a lens and aperture array with light-blocking elements in various stages of fabrication, according to an embodiment.
Figure 8B:
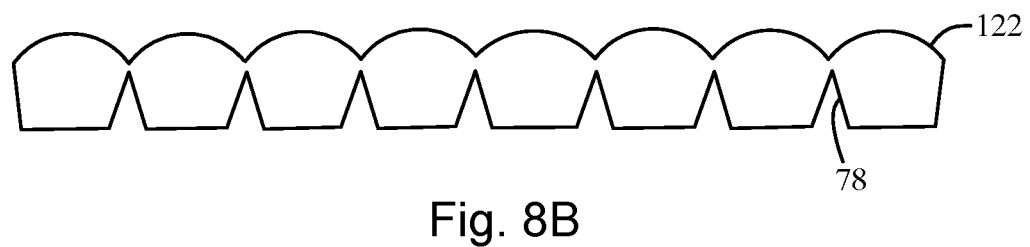
Figure 8C:
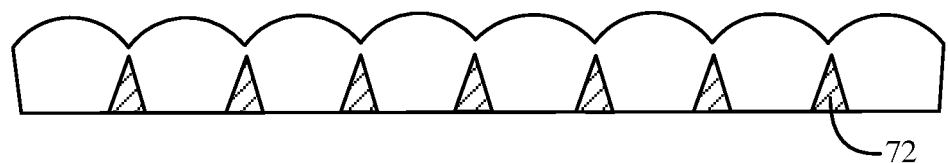
Figure 8D:
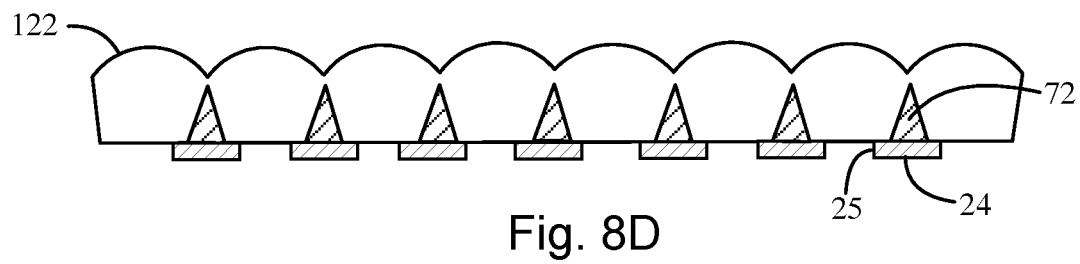

FIGS. 8A-8D depict a lens array 122 with light-blocking elements in various stages of fabrication, according to an embodiment. FIG. 8A shows a side view of the lens array 122 which may be fabricated as etched glass or molded plastic. In some embodiments, the lens array 122 is a micro-lens array commercially available from JENOPTIK Optical Systems. FIG. 8B shows cavities 78 which can be, for example, etched or integrally molded into a substrate portion 123 of the lens array 122. As shown in FIG. 8C, the cavities 78 can be filled with a substantially opaque material to form light-blocking elements 72. The light-blocking elements 72 can be constructed of, for example, black resin, metal, and/or metal film. As shown in FIG. 8D, the aperture array 24 may be positioned adjacent to the lens array 122 (with a spacer in some embodiments) such that light-blocking elements 72 are positioned between the apertures 25. In some embodiments, the aperture array 24 is constructed by patterning a metal mask on the surface of a silicon detector and positioning the detector with aperture array 24 adjacent to the lens array 22 with light-blocking elements 72 such that the light-blocking elements 72 are positioned between the between apertures 25.

Figure 9:
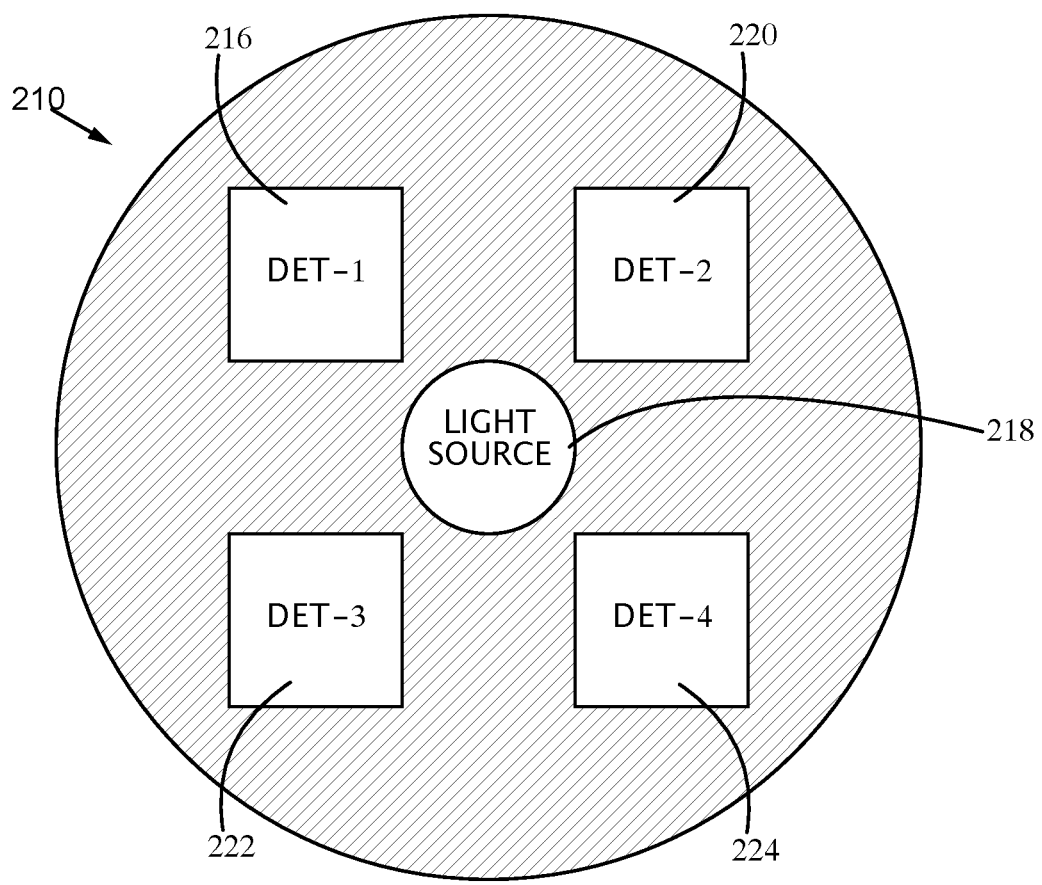
FIG. 9 is a schematic plan view of an optical detection device, according to an embodiment.

FIG. 9 is a schematic plan view of an optical detection device 210, according to an embodiment. The optical detection device 210 includes four detectors 216, 220, 222, and 224 and a light source 218. The optical detection device 210 has a relatively large ration of detector surface area to light source surface area (also referred to herein as "surface area ratio"). The large surface area ratio can improve detection of implant signals, when the implant is embedded in subcutaneous tissue (e.g., 1-4 mm under the surface of the skin). In particular, the light source 218 and four detectors 216, 220, 222, 224 are arranged such that the ratio of the surface area of the skin through which the detected light passes as it travels to the detectors 216, 220, 222, 224 to the surface area of the skin through which the excitation light is transmitted is at least 4:1. For example, in one embodiment the light source 218 has a circular cross-section and is positioned to transmit the excitation light through a substantially circular surface area of the skin having a diameter of about 3 mm, a radius of about 1.5 mm, and an excitation surface area of about 7 mm$^2$. The four detectors 216, 220, 222, 224 have square cross-sections and are positioned to detect light emitted from four substantially square surface areas of the skin, through which the detected light passes as it travels to the detectors. Each of the four detection surface areas is substantially square with sides of 3 mm, so that the total detection surface area is 4×9 mm$^2$=36 mm$^2$. Accordingly, in this example, the ratio of detection surface area to excitation surface area is slightly greater than 5:1.

In some embodiments, the optical detection device 210 can be configured to detect implant signals at a lateral distance at least twice the depth of the implant. For example, at least a portion of at least one of the detectors 216, 220, 222, 224 can be at least twice as far away from the implant laterally as that portion is from the implant distally. For example, in an instance where the light source 218 is centered over an implant that is embedded under 4 mm of tissue, at least a portion of at least one of the detectors 216, 220, 222, 224 can be 8 mm away from the center of the light source 218. Similarly stated, the furthermost edge or corner of at least one of the detectors 216, 220, 222, 224 can be at least twice as far away from the center of the light source 218 as the implant is deep. In an alternate embodiment, such as an embodiment having a single or universal detector, the detector can have a radius at least twice the depth of the implant. In other embodiments, the optical detection device 210 can be configured to detect implant signals at a lateral distance at least three times, at least five times, or any other suitable multiple of the depth of the implant. An optical detector device 210 operable to detect implant signals a relatively large lateral distance from the implant may be able to detect a larger portion of an emitted signal, particularly in a high-scattering environment. Capturing a larger portion of the emitted signal can improve detection accuracy.

Figure 10:
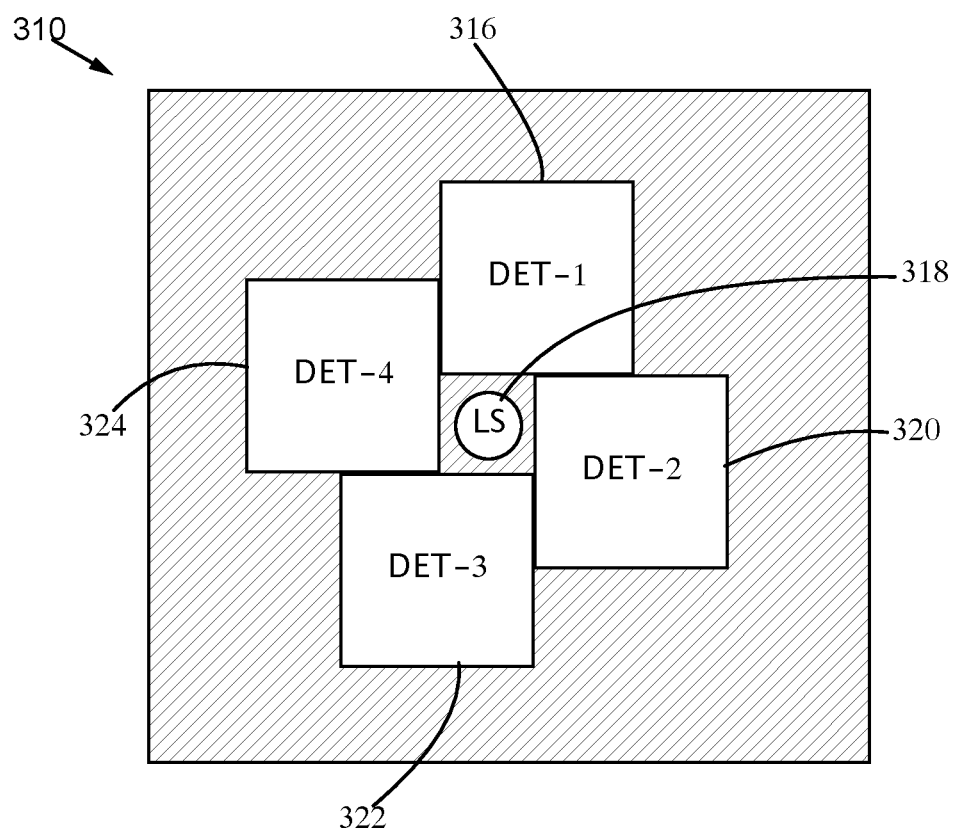
FIG. 10 is a schematic plan view of an optical detection device, according to an embodiment.

FIG. 10 is a schematic plan view of an optical detection device 310, according to an embodiment. As compared to the optical detection device 210, in this embodiment, the four detectors 316, 320, 322, 324 are positioned closer to the light source 318 as they surround or encircle the light source 318, and the ratio of detection surface area to excitation surface area is larger. For example, the light source 318 may have a circular cross-section and is arranged to transmit the excitation light through a substantially circular surface area of the skin having a diameter of about 2 mm, a radius of about 1 mm, and an excitation surface area of about 3.14 mm$^2$. The four detectors 316, 320, 322, 324 have square cross-sections and are positioned to detect light emitted from four substantially square surface areas of the skin, through which the detected light passes as it travels to the detectors. Each of the four detection surface areas is substantially square with sides of 6 mm, so that the total detection surface area is 4×36 mm$^2$=144 mm$^2$. Accordingly, in this example, the ratio of detection surface area to excitation surface area is slightly greater than 45:1.

Figure 11:
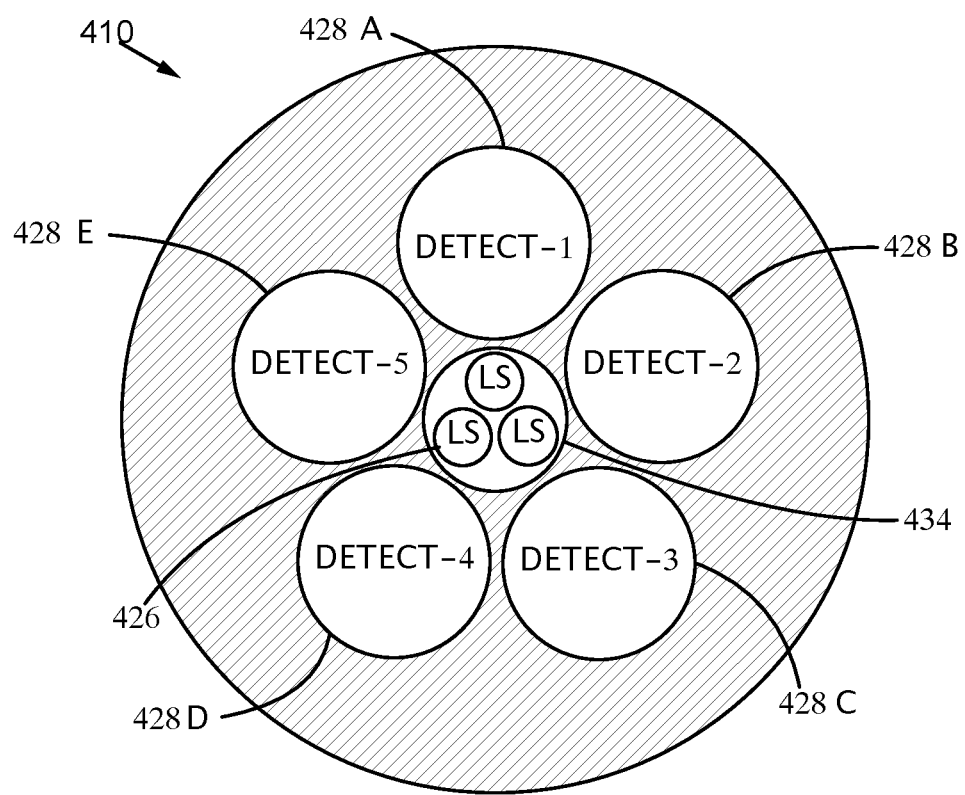
FIG. 11 is a schematic plan view of an optical detection device, according to an embodiment.

FIG. 11 is a schematic, plan view of aspects of an optical detection device 410, according to another embodiment. In this embodiment, five circular-shaped detectors 428A, 428B, 428C, 428D, and 428E surround or encircle a central via 434. The central via 434 may be a hole in the device 410. A plurality of light sources 426 are arranged to transmit excitation light in a plurality of different wavelength ranges through the central via 434. As one possible example, the light sources 426 may be arranged to transmit excitation light to the skin through the central via 434 having a circular cross-section to transmit the excitation light through a substantially circular surface area of the skin having a diameter of about 3 mm and a corresponding excitation surface area of about 7 mm$^2$. The five detectors 428A, 428B, 428C, 428D, and 428E have circular cross-sections and are positioned to detect light emitted from five substantially circular surface areas of the skin, through which the detected light passes as it travels to the detectors. Each of the five detection surface areas is substantially circular with a diameter of 5 mm, so that the total detection surface area is 5×19.6 mm$^2$=98 mm$^2$. Accordingly, in this example, the ratio of detection surface area to excitation surface area is slightly greater than 13:1.

It will be clear to one skilled in the art that the above embodiments may be altered in many ways without departing from the scope of the invention. For example, many different permutations or arrangements of one or more light sources, one or more detectors, filters, and/or light guiding elements connecting the optical components may be used to realize the device and method of the invention. For example, alternative embodiments may have different dimensions and/or wavelengths. Embodiments may include cabled or wireless hand-held readers, wireless skin patch readers, bench-top instruments, imaging systems, smartphone attachments and applications, or any other configuration that utilizes the disclosed optics and algorithms.

In some embodiments described herein, a monitoring device can be operable to simultaneously emit an excitation optical signal and detect an emission signal. For example, the detector of such a monitoring device can be shielded from reflected or back-scattering excitation light using apertures, light-blocking elements, filters, light control film, etc. In other embodiments, a monitoring device can be operable to emit an excitation optical signal during one period of time, and detect an emission signal during another period of time in which the excitation optical signal is deactivated.

Tissue optical heterogeneity in some cases may be significant. Thus, it may be advantageous to utilize a single light source and a single detector to assure that every color passes through the same optical pathway through the tissue. In one embodiment, a light source can be positioned with a set of moveable filters between the light source and the surface of the skin. Similarly a single photodetector can be utilized in place of separate discrete detector elements. The detector may be used to detect different wavelength ranges by using moveable or changeable filters to enable multiple wavelengths to be measured. Changing or moving filters may be accomplished by a mechanical actuator controlling a rotating disc, filter strip or other means. Alternatively, optical filters may be coated with a material that, when subjected to current, potential, temperature or another controllable influence, changes optical filtering properties, so that a single photodetector can serve to detect multiple wavelength ranges.

In some embodiments, the devices and methods of the present invention make use of wafer-based micro-optics. These systems are created lithographically, but can be replicated at low cost. The technology allows for layers of optics and detectors to be bonded at the wafer level and then diced into individual detector systems. Suitable components include etched refractive lenses, polymer replicated refractive lenses, etched binary lenses, replicated binary lenses, replicated holograms, and replicated volume holograms.

In some embodiments, a complementary metal-oxide-semiconductor (CMOS) detector may be used as an integral part of the optical system. The advantage of a CMOS sensor is the ability to integrate the detection, excitation, and digital filtering circuitry into a single piece of silicon. A new technology was recently announced, sCMOS, where researchers have been able to greatly reduce the noise in CMOS detectors to be comparable to charge charge-coupled device (CCD) detectors. Another benefit to a CMOS integrated solution is the ability to perform lock-in detection and digital filtering on the signals to reduce or eliminate the impact of ambient light.

While various embodiments have been described above, it should be understood that they have been presented by way of example only, not limitation, and various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

What is claimed is:

1. An apparatus, comprising:
   one or more light sources configured to transmit an excitation optical signal having an excitation wavelength through a first surface area of skin to an implanted sensor;
   one or more detectors configured to detect an analyte-dependent optical signal emitted from the implanted sensor through a second surface area of skin in response to the implanted sensor being illuminated by the excitation optical signal, the analyte-dependent optical signal having an emission wavelength, the second surface are being different from the first surface area;
   an array of lenses, each lens from the array of lenses configured to focus a mixed optical signal having a component with the excitation wavelength and a component with the emission wavelength towards onto a detector from the one or more detectors;
   at least one of a light control film or an array of apertures configured to inhibit light having an angle of incidence greater than a predetermined angle of incidence from reaching the detector; and
   a filter disposed between the one or more detectors and the at least one of the light control film or the array of apertures, the filter configured to allow the component with the emission wavelength to reach the detector, the filter configured to attenuate the component with the excitation wavelength, the filter's effectiveness at attenuating the component with the excitation wavelength decreasing with increased angle of incidence.

2. The apparatus of claim 1, wherein the array of lenses is a monolithically formed array of lenses.

3. The apparatus of claim 1, wherein the predetermined angle of incidence is a first predetermined angle of incidence, the apparatus further comprising:
   a plurality of light-blocking elements disposed within a substrate of the array of lenses, each light-blocking element from the plurality of light-blocking elements configured to inhibit a photon having an angle of incidence greater than a second predetermined angle of incidence from passing through the substrate.

4. The apparatus of claim 1, wherein each aperture from the array of apertures is aligned with a center of a lens from the array of lenses.

5. The apparatus of claim 1, further comprising:
   a cover configured to be disposed between the detector and the skin, a distance between the one or more light source and at least one detector from the one or more detectors being greater than a sum of the depth and a thickness of the cover.

6. The apparatus of claim 5, wherein the distance between the light source and at the at least one detector from the plurality of detectors is at least twice a distance between the portion of the at least one detector from the plurality of detectors and the implanted sensor.

7. The apparatus of claim 5, wherein at least a portion of at least one detector from the one or more detectors is spaced at least 2 mm from the light source.

8. The apparatus of claim 5, wherein at least one detector from the one or more detectors is less than 2 mm from the cover.

9. The apparatus of claim 5, wherein the array of lenses is disposed between the cover and the detector.

* * * * *